United States Patent [19]
Kaeding et al.

[11] 4,143,084
[45] Mar. 6, 1979

[54] DI-ALKYLBENZENE ISOMER MIXTURES

[75] Inventors: Warren N. Kaeding, Westfield; Lewis B. Young, Skillman, both of N.J.

[73] Assignee: Mobil Oil Corporation, New York, N.Y.

[21] Appl. No.: 925,585

[22] Filed: Jul. 17, 1978

Related U.S. Application Data

[63] Continuation-in-part of Ser. No. 801,177, May 27, 1977, abandoned, which is a continuation-in-part of Ser. No. 706,981, Jul. 19, 1976, Pat. No. 4,086,287.

[51] Int. Cl.$^2$ .............................................. C07C 3/52
[52] U.S. Cl. ............................. 260/671 R; 260/671 C; 260/671 P
[58] Field of Search ............ 260/668 A, 671 R, 671 P

[56] References Cited
U.S. PATENT DOCUMENTS

| | | | |
|---|---|---|---|
| 2,763,702 | 9/1956 | Amos et al. | 260/671 P |
| 2,778,862 | 1/1957 | Gorham et al. | 260/671 R |
| 2,920,119 | 1/1960 | Egbert | 260/671 R |
| 3,720,725 | 3/1973 | Olechowski | 260/671 R |

*Primary Examiner*—Veronica O'Keefe
*Attorney, Agent, or Firm*—Charles A. Huggett; Raymond W. Barclay

[57] ABSTRACT

A dialkylbenzene isomer mixture consisting essentially of ethyltoluene or diethylbenzene obtained directly by ethylation respectively of toluene or ethylbenzene and which does not require separation of the resulting isomers by prior distillation is provided, which mixture, as obtained, is substantially devoid of the ortho isomer and consists essentially of about 90 to about 99 weight percent of the para isomer and about 1 to about 10 weight percent of the meta isomer.

9 Claims, No Drawings

DI-ALKYLBENZENE ISOMER MIXTURES

CROSS REFERENCE TO RELATED APPLICATIONS

This application is a continuation-in-part of application Ser. No. 801,177 filed May 27, 1977, now abandonded, which in turn is a continuation-in-part of application Ser. No. 706,981 filed July 19, 1976, now U.S. Pat. No. 4,086,287.

BACKGROUND OF THE INVENTION

1. Field of the Invention

This invention is concerned with a dialkylbenzene isomer mixture of ethyltoluene or diethylbenzene containing in excess of about 90 weight percent of the para isomer, less than about 10 weight percent of the meta isomer and substantially devoid of the ortho isomer.

2. Description of the Prior Art

Various mixtures of dialkylbenzene isomers have heretofore been known. In these known mixtures, the para isomer has generally been present in an amount less than about 40 weight percent. Generally, the meta isomer has been present in major proportion, together with smaller amounts of the ortho isomer. Thus, U.S. Pat. No. 2,763,702 describes a mixture of ethyltoluene isomers resulting from ethylation of toluene with ethylene in the presence of a Friedel-Crafts catalyst, such as aluminum chloride, containing isomeric mono-ethyltoluenes in relative proportions of from 8 to 30 percent of the ortho isomer, 40 to 65 percent of the meta isomer and from 20 to 40 percent of the para isomer. U.S. Pat. No. 2,773,862 also describes ethylation of toluene in the presence of an aluminum chloride catalyst to yield an isomeric mixture in which the meta isomer predominates, the para isomer is present to a lesser degree and the ortho isomer is present in still smaller amount. A typical isomer mixture disclosed is one containing 10 to 20 weight percent of ortho-ethyltoluene, 25 to 30 weight percent of para-ethyltoluene and 55 to 60 weight percent of meta-ethyltoluene. U.S. Pat. No. 2,920,119 refers to a conventional ethyltoluene isomer mixture obtained by ethylation of toluene in the presence of a Friedel-Crafts catalyst as one having a meta isomer content of 72 percent, a para isomer content of 20 percent and an ortho isomer content of 8 percent. In accordance with the process of this patent, the proportion of the para isomer is increased relative to the other isomers possibly by a combination of alkylation, disproportionation and isomerization steps to yield a resulting ethyltoluene isomer mixture which may contain about 20 percent of the ortho isomer, 50 percent of the meta isomer and 30 percent of the para isomer. U.S. Pat. No. 3,720,725 discloses a reaction product mixture containing about 45 percent of ortho-ethyltoluene, about 38 percent para-ethyltoluene and about 3 percent of meta-ethyltoluene. Such reaction mixture is obtained as the result of aromatic hydrocarbon alkylation utilizing a catalyst composition comprising a molybdenum halide, an alkylaluminum dihalide and a proton donor.

While the above noted prior art is considered of interest in connection with the subject matter of the present invention, none of such prior art has disclosed an ethyltoluene or diethylbenzene isomer mixture containing from about 90 to about 99 weight percent of the para isomer, about 1 to about 10 weight percent of the meta isomer and substantially devoid, i.e., containing less than 0.1 weight percent of the ortho isomer.

Ethyltoluene and diethylbenzene are valuable chemicals. Ethyltoluene, for example, may be dehydrogenated to produce the corresponding vinyl toluene. It has heretofore been recognized that the presence of substantial quantities of the ortho isomer is highly undesirable in the charge undergoing dehydrogenation since it tends to lead to ring closure with formation of indenes and indanes which adversely effect the properties of the resultant polymer. The indenes and indanes are difficult to separate from the desired vinyl toluene. It has accordingly heretofore been necessary to remove the ortho isomer from the ethyltoluene charge stocks by expensive distillation techniques prior to dehydrogenation thereof.

It is evident that the availability of ethyltoluene or diethylbenzene in which the ortho isomer is initially absent or present only in trace amount would eliminate the necessity for expensive prior removal of this isomer. Such products have, however, not heretofore been available.

SUMMARY OF THE INVENTION

In accordance with the present invention, a dialkylbenzene isomer mixture is provided consisting essentially of about 90 to about 99 weight percent of the para isomer and about 1 to about 10 weight percent of the meta isomer and which is virtually free of the undesirable ortho isomer, thus eliminating the heretofore necessary expensive purification procedure. The ethyltoluene or diethylbenzene isomer mixture provided in accordance with the present invention contains the para isomer as the major component, present in an amount in excess of about 90 weight percent of the isomer mixture, together with minor amount of the meta isomer, less than about 10 weight percent, with only a trace or none of the ortho isomer.

The isomeric mixture of the invention is obtained by direct ethylation of toluene or ethylbenzene in the presence of a catalyst having a controlled hexane cracking activity, a minimum diffusion time for ortho-xylene and a minimum xylene sorption capacity. The zeolite catalyst used in obtaining the ethyltoluene isomer described herein, is characterized by activity, in terms of alpha value, of about 2 to about 5,000, a xylene sorption capacity of greater than 10 minutes, where the sorption capacity and sorption time are measured at 120° C. and a xylene pressure of 4.5 + 0.8 mm. of mercury.

The aforenoted ethylation of toluene or ethylbenzene is effectively accomplished at a temperature between about 250 and about 600° C. at a pressure of between about 0.1 to about 100 atmospheres utilizing a feed weight hourly space velocity (WHSV) between about 0.1 to about 100. The latter WHSV is based on the weight of catalyst composition, i.e., total weight of active catalyst and binder thereof. The molar feed ratio of toluene or ethylbenzene to ethylating agent is generally between about 1 to about 10.

DESCRIPTION OF SPECIFIC EMBODIMENTS

The dialkylbenzene isomer mixture of this invention consists essentially of about 90 to 99 weight percent of the para isomer, about 1 to about 10 weight percent of meta isomer and 0 to about 0.1 weight percent of the ortho isomer. Preferably, the para-ethyltoluene or para-diethylbenzene content is between about 97 and about 99 weight percent and the meta-ethyltoluene or diethylbenzene content is between about 1 and about 3 weight percent. Still more preferably, the para-ethyltoluene or para diethylbenzene content is between about 98 and about 99 weight percent and the meta-ethyltoluene or meta diethylbenzene content is between about 1 and about 2 weight percent.

A particular advantage of the isomer mixture described herein is that it does not require separation of the isomers by prior distillation. As will be realized, the dialkylbenzene isomer mixture, constituting the subject matter of this invention, eliminates extraction or crystallization techniques which have heretofore been necessary in obtaining dialkylbenzenes, such as ethyltoluene or diethylbenzene free from the ortho isomer.

The isomer mixture of the invention is obtained by ethylation of toluene or ethylbenzene by contacting with an ethylating agent, under conversion conditions, in the presence of a catalyst having controlled hexane cracking activity, a minimum diffusion time for ortho-xylene and a minimum xylene sorption capacity. More particularly, the zeolite utilized herein as catalyst is characterized by an activity, in terms of alpha value, of between about 2 and about 5000, a xylene sorption capacity of greater than 1 gram/100 grams of zeolite and an ortho-xylene sorption time of greater than 10 minutes for 30 percent of said capacity, where the sorption capacity and sorption time are measured at 120° C. and a xylene pressure of 4.5 + 0.8 mm. of mercury.

The ethylating agent employed is generally ethylene or a gaseous mixture high in this reactant. Other suitable ethylating agents include ethyl alcohol and ethyl halides, e.g., ethyl chloride, diethyl ether, diethyl sulfide and ethylmercaptan.

The above-described reactants are brought into contact, under conversion conditions, with bed comprising particle-form catalyst containing a crystalline aluminosilicate having: (1) an activity, in terms of alpha value, of between about 2 and about 5,000 (2) a xylene sorption capacity greater than 1 gram/100 grams of zeolite and (3) an ortho-xylene sorption time of greater than 10 minutes for 30 percent of said capacity, where the sorption capacity and sorption time are measured at 120° C. and a xylene pressure of 4.5 + 0.8 mm. of mercury.

The alpha value reflects the relative activity of the catalyst with respect to a high activity silica-alumina cracking catalyst. To determine the alpha value as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e., the silica-alumina standard. The silica-alumina reference catalyst contains about 10 weight percent $Al_2O_3$ and remainder $SiO_2$. This method of determining alpha, modified as described above, is more fully described in the Journal of Catalysis, Vol. VI, Pages 278–287, 1966.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5 + 0.8 mm. of mercury and an ortho-xylene sorption time for 30 percent of said capacity of greater than 10 minutes (at the same conditions of temperatures and pressure) are required in order to achieve the desired selected production of para-ethyltoluene.

It has been found that zeolites exhibiting very high selectivity for para-ethyltoluene or para diethylbenzene production require a very long time up to and exceeding a thousand minutes to sorb o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

$$t_{0.3} = F \cdot t_{0.05}$$

| Percent of sorption capacity | Factor(F) to Estimate 30% Sorption Time |
|---|---|
| 5 | 36 |
| 10 | 9 |
| 20 | 2.2 |

The zeolite catalysts utilized herein are members of a novel class of zeolites exhibiting some unusual properties. The zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 100% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| Clinoptilolite | 3.4 |
| TMA Offretite | 3.7 |
| Beta | 0.6 |

| CAS | C.I. |
| --- | --- |
| -continued | |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such as the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural mineral which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen from of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, —11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The crystalline aluminosilicate zeolites employed are modified prior to use by combining therewith a small amount, generally in the range of about 0.5 to about 40 weight percent, preferably of a difficulty reducible oxide, such as the oxides of phosphorus, boron, magnesium or combinations thereof and also oxides of antimony. Modification of the zeolite with the desired oxide or oxides can readily be effected by contacting the zeolite with a solution of an appropriate compound of the element to be introduced, followed by drying and calcining to convert the compound to its oxide form.

Representative phosphorus-containing compounds which may be used include derivatives of groups represented by $PX_3$, $RPX_2$, $R_3P$, $X_3PO$, $(XO_3)PO$, $(XO)_3P$, $R_3P=O$, $R_3P=S$, $RPO_2$, $POS_2$, $RP(O)(OX)_2$, $RP(S)(SX)_2$, $R_2O(O)X$, $R_2O(S)SX$, $RP(OX)_2$, $RP(SX)_2$, $ROP(OX)_2$, $(RS)_2PSP(SR)_2$, and $(RO)_2POP(OR)_2$, where R is an alkyl or aryl, such as phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $(RP(O)-(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous cid, primary, (RO)P(OX)$_2$, secondary, (RO)$_2$POX, and tertiary, (RO)$_3$P, phosphites; and esters thereof such as the monopropyl ester, alkyl dialkylphosphinites, (RO)PR$_2$, and dialkyl alkylphosphonite, (RO)$_2$PR esters. Corresponding sulfur derivatives may also be employed including (RS)$_2$P(S)H, (RS)$_2$P(S)R, (RS)P(S)R$_2$, R$_2$OSX, (RS)P(SX)$_2$, (RS)$_2$PSX, (RS)$_3$P, (RS)PR$_2$ and (RS)$_2$PR. Examples of phosphite esters include trimethylphosphite, triethylphosphite diisopropylphosphite, butylphosphite; and pyrophosphites such as tetraethylpyrophosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, (RO)PCl$_2$, dialkyl phosphorochloridites, (RO)$_2$PX, dialkylphosphionochlorides, R$_2$PCl, alkyl alkylphosphonochloridates, (RO)(R)P(O)Cl, dialkyl phosphinochloridates, R$_2$P(O)Cl and RP(O)Cl$_2$. Applicable corresponding sulfur derivatives include (RS)PCl$_2$, (RS)$_2$PX, (RS)(R)P(S)Cl and R$_2$P(S)Cl.

Preferred phosphorus-containing compounds include diphenyl phosphine chloride, trimethylphosphite and phosphorus trichloride, phosphoric acid, ammonium phosphate, phenyl phosphine oxychloride, trimethylphosphate, diphenyl phosphinous acid, diphenyl phosphinic acid, diethylchloro thiophosphate, metyl acid phosphate and other alcohol-P$_2$O$_5$ reaction products.

Reaction of the zeolite with the phosphorus compound is effected by contacting the zeolite with such compound. Where the treating phosphorus compound is liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of phosphorus incorporated with the zeolite should be at least bout 0.5 percent by weight. However, it is preferred that the amount of phosphorus in the zeolite be at least about 2 percent by weight when the same is combined with a binder, e.g., 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time. i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction temperature, the degree to which the zeolite has been dried prior to reaction with the phosphorus-containing compound, the conditions of drying of the zeolite after reaction of the zeolite with the treating compound, and the amount and type of binder incorporated with the zeolite.

Another suitable modifying oxide is that of magnesium. Representative magnesium-containing compounds include magnesium acetate, magnesium nitrate, magnesium benzoate, magnesium proprionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium silicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound is in the gaseous phase, it can be used by itself or can be used in admixture with a gaseous diluent relatively inert to the treating compound and the zeolite such as helium or nitrogen or with an organic solvent, such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, i.e., up to about 500° C. are preferred. Heating is generally carried out for 1–5 hours but may be extended to 24 hours or longer. While heating temperatures above about 500° C. may be employed, they are generally not necessary. At temperatures of about 1000° C., the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g., 35 weight percent of alumina. The amount of magnesium oxide can be as high as about 25 percent by weight or more depending on the amount and type of binder present. Preferably, the amount of magnesium oxide added to the zeolite is between about 1 and about 15 percent by weight.

Boron oxide is also an effective modifying component. Representative boron-containing compounds include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron and allylborate.

Reaction of the zeolite with the boron compound is effected by contacting the zeolite with such compound. Where the treating boron compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the boron-containing compound is, for example, trimethylborate, a hydrocabon solvent such as n-octane may be employed. The boron-containing compound may be used without a solvent, i.e., may be used as a neat liquid. Where the boron-containing compound is in the gaseous phase, such as where gaseous diborane is employed, the treating compound can be used by itself or can be used in admixture with a gaseous diluent inert to the boron-containing compound and the zeolite such as nitrogen or helium or with an organic solvent, such as octane.

Prior to reacting the zeolite with the boron-containing compound, the zeolite may be dried. Drying can be effected in the presence of air. Elevated temperatures may be employed. However, the temperature should not be such that the crystal structure of the zeolite is destroyed.

Heating of the boron-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 3-5 hours but may be extended to 24 hours or longer. While heating temperatures above about 500° C. can be employed, they are not necessary. At temperatures of about 1000° C., the crystal structure of the zeolite tends to deteriorate.

The amount of boron incorporated with the zeolite should be at least about 0.2 percent by weight. However, it is preferred that the amount of boron in the zeolite be at least about 1 percent by weight when the same is combined with a binder, e.g., 35 weight percent of alumina. The amount of boron can be as high as about 20 percent by weight or more depending on the amount and type of binder present. Preferably, the amount of boron added to the zeolite is between about 1.5 and 10 percent by weight. Without being limited by any theoretical considerations, it is contemplated that boron is actually present in the zeolite in an oxidized state, such as $B_2O_3$.

Antimony oxide may also be employed as a modifying component. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $SB_2O_3$. Generally, the amount of $Sb_2O_3$ in the composite catalyst will be between about 6 and about 40 weight percent and preferably between about 10 and about 35 weight percent. Antimony derivatives which may be used include: the hydrides $SbH_3$; the halides $MX_3$, $MX_5$(M = Sb, X = F, Cl, Br, I); organic alkyl and aryl stibines and their oxides $R_3Sb$, $R_5Sb$, $R_xSb=O$ (R-alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)_6$; organic acids such as $RSbO(OH)_2$, $R_2SbO \cdot OH$, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$; $Sb(OCH_3)_3$; and antimonyl salts as $(SbO)SO_4$, $(SbO)NO_3$, $K(SbO)C_4H_4O_6$, $HaSbO_2 \cdot 3H_2O$.

In some instances, it may be desirable to modify the crystalline aluminosilicate zeolite by combining therewith two or more of the specified oxides. Thus, the zeolite may be modified by prior combination therewith of oxides of phosphorus and boron, oxides of phosphorus and magnesium or oxides of magnesium and boron. When such modification technique is employed, the oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 0.5 and about 40 weight percent.

Still another modifying treatment entails steaming of the zeolite by contact with an atmosphere containing from about 5 to about 100 percent steam at a temperature of from about 250 to about 1000° C. for a period of between about 0.25 and about 100 hours and under pressures ranging from sub-atmospheric to several hundred atmospheres to reduce the alpha value thereof to less than 500 and preferably less approximate than 20 but greater than zero.

Another modifying treatment involves precoking of the catalyst to deposit a coating of between about 2 and about 75 and preferably between 15 and about 75 weight percent of coke thereon. Precoking can be accomplished by contacting the catalyst with a hydrocarbon charge, e.g., toluene, under high severity conditions or alternatively at a reduced hydrogen to hydrocarbon concentration, i.e., 0 to 1 mole ratio of hydrogen to hydrocarbon for a sufficient time to deposit the desired amount of coke thereon.

It is also contemplated that a combination of steaming and precoking of the catalyst under the above conditions may be employed to suitably modify the crystalline aluminosilicate zeolite catalyst.

The conversion process desscribed herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g., air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5-2%) is used to burn the coke in a controlled manner so as to limit the temperature to a maximum of around 500–550° C.

The following examples wherein the modified zeolites are characterized by an activity, in terms of alpha value, of between about 2 and about 5000, and preferably between about 20 and about 500, a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 + 0.8 mm. of mercury, will serve to illustrate the isomer mixture of the invention and preparation thereof without limiting the same.

EXAMPLE 1

Twenty grams of the ammonium form of ZSM-5 was suspended in a solution of 6.69 grams of boric acid $H_3BO_3$, in 40 ml. of hot water and allowed to stand overnight at a temperature of about 90° C. The slurry was then placed in an oven at 115° C. and slurried every 30 minute to maintain uniformity as the water evaporated. After about 2 hours, the bulk of the water was removed and the temperature was increased to 200° C. After about 5 hours, the catalyst weight was 32.4 grams. It was then placed in a furnace, in air, at 500° C., overnight. After cooling the catalyst weight was 21.95 grams, having a theoretical boron content of 4.9 weight percent.

EXAMPLE 2

Toluene and ethylene in a mole ratio of 5.3 (toluene-/ethylene) were passed over a catalyst prepared as in Example 1 at a temperature of 450° C. and atmospheric pressure at a weight hourly space velocity of 5.3. Toluene conversion was 6.8 percent (36 percent of theory). Conversion products, on a mole percent basis, were as follows:

| | |
|---|---|
| Benzene | 6 |
| Ethylbenzene | 3 |
| Xylenes | 11 (para:meta:ortho = 69:21:10) |
| Ethyltoluenes | 79 (para:meta:ortho = 94: 6: 0) |
| Other $C_9$ | 1 |

It is noteworthy that ethyltoluenes containing 94 percent of the para isomer were obtained.

EXAMPLE 3

A six gram sample of the ammonium form of ZSM-5 was treated with a solution of 7 grams of magnesium acetate tetrahydrate, dissolved in 15 ml of water. The suspension was heated to 92° C. and permitted to stand overnight. The slurry was poured into a crystallizing dish and placed in a 110° C. over for a period of about 7 hours. The temperature was then increased to about 200° C. and allowed to stand for an additional hour. The catalyst was then placed in a furnace at 500° C. overnight. The weight of the catalyst at the end of this treatment was 6.68 grams. Analysis showed it to have an Mg content of 10.1 weight percent.

EXAMPLE 4

Toluene was alkylated with ethylene in the presence of the catalyst of Example 3. The conditions of reaction and analytical results are summarized in Table I below.

TABLE I

| Run No. | 1 | 2 | 3 |
|---|---|---|---|
| Temp. ° C. | 350 | 400 | 450 |
| WHSV | 7.4 | 7.4 | 7.4 |
| Molar Feed Ratio | | | |
| Toluene/Ethylene | 5.1 | 5.1 | 5.1 |
| Stream Time, Hrs. | 1 | 2 | 3 |
| Conversion Toluene | 12.6 | 13.2 | 10.0 |
| Wt. % Ethylene | 65.2 | 60.3 | 43.6 |
| Ethyl Toluene | | | |
| Para | 98.99 | 98.38 | 97.83 |
| Meta | 1.01 | 1.62 | 2.17 |
| Ortho | 0 | .027 | .049 |

From the above results, it will be seen that the selectivity to para-xylene was exceptionally high, with only minute amounts of the ortho isomer being produced.

EXAMPLE 5

HZSM-5 having a crystallite size of 0.02 to 0.05 micron was mixed with 35 weight percent alumina binder and extruded to produce a 1/16′ cylindrical particle. A ten gram sample of this extrudate was soaked overnight at room temperature in a solution of 8 grams of 85% phosphoric acid in 10 ml of water. The resulting product was filtered, dried at 120° C. for about 2 hours and calcined at 500° C. for approximately an additional 2 hours. Ten grams of the phosphorus impregnated extrudate was then soaked at room temperature overnight in a solution of 25 grams of magnesium acetate tetrahydrate in 20 ml of water. It was then filtered, dried at 120° C. for about 2 hours and the placed in a furnace at 500° C. for approximately 2 hours. The resulting product contained 4.18 weight percent phosphorus and 7.41 weight percent magnesium.

EXAMPLE 6

Toluene was alkylated with ethylene in the presence of the catalyst of Example 5. The conditions of reaction and analytical results are summarized in Table II below.

TABLE II

| Run No. | 1 | 2 | 3 | 4 | 5 | 6 | 7 |
|---|---|---|---|---|---|---|---|
| Temp. ° C. | 300 | 350 | 350 | 350 | 400 | 400 | 450 |
| WHSV | 7.4 | 7.4 | 3.9 | 3.9 | 3.9 | 3.9 | 3.9 |
| Molar Feed Ratio | | | | | | | |
| Toluene/Ethylene | 5.1 | 5.1 | 2.5 | 2.5 | 2.5 | 2.5 | 2.5 |
| Stream Time, Hrs. | 1 | 2 | 3 | 4 | 5 | 6 | 7 |
| Conversion Toluene | 2.4 | 7.1 | 8.2 | 9.2 | 8.0 | 20.1 | 13.2 |
| Wt. % Ethylene | 1.6 | 29.3 | 17.2 | 55.1 | 12.7 | 59.9 | 2.1 |
| Ethyl Toluene | | | | | | | |
| Para | 100 | 100 | 99.2 | 98.6 | 98.04 | 98.96 | 98.84 |
| Meta | — | — | .8 | 1.4 | 1.88 | 1.04 | 1.16 |
| Ortho | — | — | — | — | .08 | .04 | — |

Catalyst calcined between runs 3 and 4 and between runs 5 and 6.

EXAMPLE 7

A 12 gram sample of the ammonium form of ZSM-5 having a crystallite size of about 2 microns was suspended in a solution of 14 grams of magnesium acetate tetrahydrate and 0.8 gram of boric acid dissolved in 25 ml of water. The suspension was heated to 88° C., permitted to stand overnight and then heated in an oven at 110° C. for a period of about 8 hours. It was thereafter placed in a furnace at 500° C. overnight. The weight of the resulting catalyst product was 14.93 grams. It had a magnesium content (theory) of 9.3 weight percent and a boron content (theory) of 2.6 weight percent.

EXAMPLE 8

The catalyst of Example 7 was used to alkylate toluene with ethylene. The conditions of reaction and analytical results are summarized in Table III below.

TABLE III

| Run No. | 1 | 2 | 3 | 4 |
|---|---|---|---|---|
| Temp. °C. | 350 | 350 | 400 | 400 |
| WHSV | 7.4 | 4.0 | 7.4 | 4.0 |
| Molar Feed Ratio | | | | |
| Toluene/Ethylene | 4.5 | 2.2 | 4.5 | 2.2 |
| Stream Time, Hrs. | 1 | 2 | 3 | 4 |
| Conversion Toluene | 8.7 | 8.6 | 4.9 | 10.6 |
| Wt. % Ethylene | 49.9 | 38.2 | 25.9 | 40.1 |
| Ethyl Toluene | | | | |
| Para | 94.8 | 94.1 | 91.0 | 90.6 |
| Meta | 5.2 | 5.9 | 9.0 | 9.4 |
| Ortho | — | — | — | — |

It will be evident from the above results that very high yields of para ethyltoluene were obtained, with no ortho ethyltoluene being detected in the product mixture.

EXAMPLE 9

A 5.3 gram sample of the hydrogen form of ZSM-5 having a crystallite size of about 2 micron was steamed at 515° C. for a period of 2 hours and a feed rate of 8.8 cc of liquid water per hour. The temperature was then raised to 640° C. Toluene was then fed at a rate of 180 ml per hour for a period of 4 hours and 15 minutes. The temperature was then reduced to 550° C., the catalyst flushed with nitrogen and then cooled to yield a coke-containing product.

EXAMPLE 10

Toluene was alkylated with ethylene in the presence of the catalyst of Example 9. The conditions of reaction included a temperature of 300° C., a weight hourly space velocity of 7.4, a molar feed ratio of toluene to ethylene of 5 and a stream time of one hour. The conversion of toluene obtained was 4.1 weight percent and of ethylene 24.1 weight percent. The ethyltoluene isomer mixture was found to contain 93.15 weight percent of para isomer and 6.85 weight percent of the meta isomer.

EXAMPLE 11

A 4 gram sample of the hydrogen form of ZSM-5 having a crystallite size of about 2 microns was pressed into wafers and sized to 14–20 mesh particles. The resulting material was placed in a quartz microreactor and treated with steam at 600° C. for 7 hours.

EXAMPLE 12

Ethylbenzene was alkylated with ethylene in the presence of the catalyst of Example 11. The condition of reaction included a temperature of 400° C., a weight hourly space velocity (ethylbenzene/ethylene) of 4.29/0.17 hr$^{-1}$. The conversion of ethylbenzene was 27 weight percent. Seventy percent of the product consisted of diethylbenzenes with a para/meta/ortho isomer ratio of 68/32/<0.5.

In contrast to the results obtained above, the following examples are representative of the prior method for ethylation of toluene or ethylbenzene utilizing a Friedel-Crafts catalyst, e.g., aluminum chloride:

EXAMPLE 13

To 100 ml of toluene was added 1 gram of aluminum chloride and ethylene at a rate of 40 cc/minute at a temperature of 80° C. After 2 hours, the composition was that shown in Table IV below:

TABLE IV

| Component | Weight Percent |
|---|---|
| Benzene | 0.20 |
| Toluene | 71.90 |
| Ethylbenzene | 0.17 |
| Xylene | |
| Para | 0.15 |
| Meta | 0.06 |
| Ortho | 0.04 |
| Ethyl Toluene | |
| Para | 6.43 |
| Meta | 14.37 |
| Ortho | 3.24 |
| Higher | 1.45 |
| Other | 1.99 |

The para/metha/ortho ethyltoluene ratio was 27/60/13.

EXAMPLE 14

To 50 ml of ethylbenzene was added 1 gram of aluminum chloride and ethylene at a rate of 10 cc/minute at a temperature of 40° C. After 0.8 hours, the composition was as shown in Table V below:

TABLE V

| Component | Weight Percent |
|---|---|
| Benzene | 11.45 |
| Toluene | 0.10 |
| Ethylbenzene | 65.37 |
| Diethylbenzene | |
| Para | 7.77 |
| Meta | 11.35 |
| Ortho | 1.53 |
| Triethylbenzenes | 2.20 |
| Other | 0.23 |

The para/meta/ortho - diethylbenzene isomer ratio was 38/55/7. In addition, it will be evident that a sizeable amount of triethylbenzenes were formed.

It will be evident from the foregoing examples illustrative of the invention that an ethyltoluene or diethylbenzene isomer mixture, constituting the product of this invention, consisting essentially of 90 to 99 weight percent of the para isomer, about 1 to about 10 weight percent of the meta isomer and substantially devoid of the ortho isomer, is achieved by ethylation of toluene or ethylbenzene by utilizing the modified crystalline aluminosilicate zeolite catalysts disclosed herein.

What is claimed is:

1. A dialkylbenzene isomer mixture consisting essentially of ethyltoluene or diethylbenzene obtained directly by ethylation respectively of toluene or ethylbenzene and which does not require separation of the resulting isomers by prior distillation is provided, which mixture, as obtained, is substantially devoid of the ortho isomer and consists essentialy of about 90 to about 99 weight percent of the para isomer and about 1 to about 10 weight percent of the meta isomer.

2. The dialkylbenzene isomer mixture of claim 1 wherein the para isomer content is between 97 and 99 weight percent and the meta isomer content is between 1 and 3 weight percent.

3. The dialkylbenzene isomer mixture of claim 1 wherein the para isomer content is between 98 and 99 weight percent and the meta isomer content is between 1 and 2 weight percent.

4. The dialkylbenzene isomer mixture of claim 1 wherein said mixture consists essentially of ethyltoluene.

5. The dialkylbenzene isomer mixture of claim 1 wherein said mixture consists essentially of diethylbenzene.

6. The ethyltoluene isomer mixture of claim 4 wherein the para isomer content is between 97 and 99 weight percent and the meta isomer content is between 1 and 3 weight percent.

7. The ethyltoluene isomer mixture of claim 4 wherein the para isomer content is between 98 and 99 weight percent and the meta isomer content is between 1 and 2 weight percent.

8. The diethylbenzene isomer mixture of claim 5 wherein the para isomer content is between 97 and 99 weight percent and the meta isomer content is between 1 and 3 weight percent.

9. The diethylbenzene isomer mixture of claim 5 wherein the para isomer content is between 98 and 99 weight percent and the meta isomer content is between 1 and 2 weight percent.

* * * * *

UNITED STATES PATENT AND TRADEMARK OFFICE
CERTIFICATE OF CORRECTION

PATENT NO. : 4,143,084
DATED : March 6, 1979
INVENTOR(S) : WARREN N. KAEDING and LEWIS B. YOUNG It is certified that error appears in the above-identified patent and that said Letters Patent are hereby corrected as shown below:

Column 2    Line 55    -    "thereof" should be --therefor--.

Column 5    Line 39    -    "100" should be --10--.

Column 12   Line  3    -    "SB$_2$O$_3$" should be --Sb$_2$O$_3$--.

*Signed and Sealed this*

*Tenth* Day of *July 1979*

[SEAL]

*Attest:*

*Attesting Officer*   LUTRELLE F. PARKER
         *Acting Commissioner of Patents and Trademarks*